(12) United States Patent
Saad

(10) Patent No.: US 11,744,975 B2
(45) Date of Patent: Sep. 5, 2023

(54) METHOD OF MANUFACTURING AN ANESTHESIA FACE MASK

(71) Applicant: Koo Medical Equipment (Shanghai) Co., Ltd., Shanghai (CN)

(72) Inventor: Steven Saad, Knoxville, TN (US)

(73) Assignee: KOO MEDICAL EQUIPMENT (SHANGHAI) CO., LTD., Shanghai (CN)

( * ) Notice: Subject to any disclaimer, the term of this patent is extended or adjusted under 35 U.S.C. 154(b) by 789 days.

(21) Appl. No.: 16/663,405

(22) Filed: Oct. 25, 2019

(65) Prior Publication Data

US 2021/0061963 A1 Mar. 4, 2021

(51) Int. Cl.
*A61M 16/06* (2006.01)

(52) U.S. Cl.
CPC ........ *A61M 16/0622* (2014.02); *A61M 16/06* (2013.01); *A61M 2207/00* (2013.01); *A61M 2207/10* (2013.01); *A61M 2210/0606* (2013.01)

(58) Field of Classification Search
CPC .......... A61M 16/0084; A61M 16/0622; A61M 16/06; A61M 16/0605; A61M 16/0616; A61M 2207/00
See application file for complete search history.

(56) References Cited

U.S. PATENT DOCUMENTS

| | | | |
|---|---|---|---|
| 6,408,853 B1 * | 6/2002 | Chang | A61M 16/0605 128/203.29 |
| D499,803 S | 12/2004 | Chang | |
| 7,290,546 B2 | 11/2007 | Sprinkle et al. | |
| D582,031 S | 12/2008 | Sorensen et al. | |
| 7,575,006 B2 | 8/2009 | Schegerin | |
| 7,621,274 B2 | 11/2009 | Sprinkle et al. | |
| 8,028,698 B2 | 10/2011 | Hodos et al. | |
| 8,336,549 B2 * | 12/2012 | Nashed | A61M 16/0605 128/203.29 |
| 8,413,656 B2 * | 4/2013 | Warren | A61M 16/06 128/206.25 |
| RE44,545 E | 10/2013 | Schegerin | |
| 9,044,562 B2 | 6/2015 | Dillingham et al. | |
| 9,072,852 B2 * | 7/2015 | McAuley | A61M 16/06 |
| D753,287 S | 4/2016 | Darab | |
| D766,422 S | 9/2016 | Svoboda et al. | |

(Continued)

FOREIGN PATENT DOCUMENTS

WO WO2005002656 1/2005

*Primary Examiner* — Joseph D. Boecker
*Assistant Examiner* — Thomas W Greig
(74) *Attorney, Agent, or Firm* — Robinson IP Law, PLLC

(57) ABSTRACT

Methods of manufacturing a mask include: providing a shell having an inlet formed on a body of the shell and a flange formed around a lower end of the body, the flange forming a surface on a bottom thereof; providing a first film substrate; providing a second film substrate; bonding the first film substrate to the second film substrate around an outer edge and around an inner edge shaped to fit around a nose and mouth of a patient; cutting the first film substrate and the second film substrate around the outer edge and the inner edge of the first film substrate and the second film substrate. The bonded and cut first film substrate and second film substrate form a first sheet that is joined to a second sheet. The shell is joined to the first sheet at the surface formed on the bottom of the flange.

16 Claims, 6 Drawing Sheets

(56) References Cited

U.S. PATENT DOCUMENTS

| | | | |
|---|---|---|---|
| D779,651 S | 2/2017 | Luchterhand et al. | |
| 10,052,448 B2 | 8/2018 | Barlow et al. | |
| 10,821,250 B2* | 11/2020 | Siew | A61M 16/0666 |
| 2002/0134388 A1* | 9/2002 | Chang | A61M 16/0683 |
| | | | 128/206.21 |
| 2004/0182398 A1 | 9/2004 | Sprinkle et al. | |
| 2004/0211428 A1* | 10/2004 | Jones, Jr. | A61M 16/06 |
| | | | 128/206.27 |
| 2005/0011521 A1 | 1/2005 | Sprinkle et al. | |
| 2005/0016532 A1* | 1/2005 | Farrell | A61M 16/0048 |
| | | | 128/202.28 |
| 2006/0081240 A1* | 4/2006 | Chang | A61M 16/06 |
| | | | 128/200.24 |
| 2006/0130845 A1 | 6/2006 | Schegerin | |
| 2008/0041388 A1* | 2/2008 | McAuley | A61M 16/0622 |
| | | | 128/206.24 |
| 2011/0146684 A1* | 6/2011 | Wells | A61M 16/06 |
| | | | 128/205.25 |
| 2012/0255554 A1 | 10/2012 | Warren | |
| 2015/0075532 A1* | 3/2015 | Patel | C08L 23/06 |
| | | | 128/206.24 |
| 2015/0343162 A1* | 12/2015 | Svoboda | A61M 16/06 |
| | | | 128/206.27 |
| 2017/0049983 A1* | 2/2017 | Ellis | B32B 3/266 |
| 2019/0209799 A1* | 7/2019 | Ovzinsky | A61M 16/0605 |

\* cited by examiner

METHOD OF MANUFACTURING AN ANESTHESIA FACE MASK

CROSS-REFERENCE TO RELATED APPLICATION

This application claims priority to Chinese Patent Application No. 201910823665.5 filed on Sep. 2, 2019, the contents of which are incorporated herein by reference in its entirety.

FIELD

This disclosure relates to the field of medical devices and methods of manufacturing medical devices. More particularly, this disclosure relates to an anesthesia mask and methods of manufacturing an anesthesia mask.

BACKGROUND

Anesthesia masks serve as an interface between an anesthesia circuit and a patient such that anesthesia may be administered to the patient. An upper portion of an anesthesia mask typically provides a standard connection to the anesthesia circuit, while a bottom is typically pliable such that an airtight seal is created that encompasses the patient's mouth and nose. The seal must be airtight and prevent anesthesia gases from escaping to the surrounding atmosphere such that anesthesia is properly administered to the patient. It is desired that the clinician be able to easily and quickly attain an airtight seal to the patient's face for the safety of patient and caregivers and to reduce costs associated with improper administration of anesthesia.

Anesthesia masks are usually typically formed having two parts: a shell and an air cushion. The shell is bonded to the air cushion at a planar surface of the shell. The planar surface is to minimize processing time and expense of bonding the shell to the cushion. Cushions for anesthesia masks are primarily made using one of two methods: rotational molding of a PVC compound and blow molding of a PVC compound. An optional air valve is in fluid communication with the air bladder to allow a user to add or subtract air from the cushion. A third type of anesthesia mask is made entirely of injection molded parts and has no air bladder. A soft pliable, plastic is bonded to the more rigid shell and serves as the patient contact surface.

Various drawbacks exist with respect to current methods of manufacturing masks as described above. For example, while rotational molding is considered to produce comfortable masks, controlling a thickness of the mark, particularly in areas where a thickness may be desired to be thin in contact with the patient. Further, rotational molding is high in cost and further requires a greater amount of material to be used in manufacturing of the mask. A side of the air cushion secured to the shell must also be thick to provide a surface for bonding the air cushion to the shell. Rotational molding is also a slow process and defects are common.

Manufacturing masks by blow molding the air cushion portion also has significant disadvantages. For example, although blow molding the air cushion is faster and less expensive relative to rotational molding, the cushion is generally thicker and less pliable than manufacturing masks using rotational molding. Further, a thicker and less pliable cushion surface makes creation of a sufficient seal against the patient's face difficult. Blow molding the air cushion also requires more material due to the thickness of the air cushion.

Finally, while masks may be formed using an all-injection molding process, significant disadvantages also exist. While frequently the least expensive method of manufacturing masks, the surface of the mask contacting the patient is the least pliable and makes attaining an air-tight seal against the patient's face difficult.

What is needed, therefore, is a method of manufacturing an anesthesia mask for use with patients that is inexpensive while also producing a mask that is effective in creating a sufficient seal against the patient's face for administration of anesthesia.

SUMMARY

In a first aspect, a method of manufacturing a mask includes: providing a shell having an inlet formed on a body of the shell and a flange formed around a lower end of the body, the flange forming a surface on a bottom thereof; providing a first film substrate; providing a second film substrate; aligning the first film substrate with the second film substrate; bonding the first film substrate to the second film substrate around an outer edge and around an inner edge, the inner edge shaped to fit around a nose and mouth of a patient; cutting the first film substrate and the second film substrate around the outer edge and the inner edge of the first film substrate and the second film substrate such that a cutout is formed within the inner edge of the first film substrate and the second film substrate. The bonded and cut first film substrate and second film substrate form a first sheet that is joined to a second sheet. The shell is joined to the first sheet at the surface formed on the bottom of the flange.

In one embodiment, the shell is formed of a plastic that is more rigid than the material of the first film substrate and the second film substrate. In another embodiment, the thickness of the first film substrate is greater than a thickness of the second film substrate such that the first sheet is thicker than the second sheet. In yet another embodiment, the first film substrate and the second film substrate comprise blow molded TPU film.

In one embodiment, the bonding and cutting of the first film substrate to the second film substrate around the outer edge and the inner edge occurs simultaneously. In another embodiment, the shell further includes an air valve formed in the body of the shell. In yet another embodiment, the method further includes piercing an aperture in the first sheet such that the aperture is in alignment with the air valve of the shell when the first sheet is joined to the flange of the shell.

In one embodiment, the cutout within the inner edge includes a mouth portion and a nose contour such that the cutout fits around the nose and mouth of the patient. In another embodiment, the first film substrate and the second film substrate are formed of a material selected from the group consisting of TPU, PVC, EVA, and combinations thereof.

In yet another embodiment, the bonding of the first film substrate and the second film substrate is performed by melting the first film substrate to the second film substrate along the outer edge and inner edge. In one embodiment, the bonding of the first film substrate and the second film substrate is performed by ultrasonic welding of the first film substrate to the second film substrate along the outer edge and the inner edge.

In another embodiment, the first film substrate and the second film substrate have a thickness of from about 0.02 mm and 0.2 mm. In yet another embodiment, the first film substrate has a thickness of from about 0.08 mm and about 0.12 mm and the second film substrate has a thickness of from about 0.03 mm to about 0.07 mm. In one embodiment, the first film substrate has a thickness of approximately 0.1 mm and the second film substrate having a thickness of approximately 0.05 mm.

In a second aspect, a method of manufacturing a mask includes: providing a shell having an inlet formed on a body of the shell and a flange formed around a lower end of the body, the flange forming a surface on a bottom thereof; providing a first film substrate having a first thickness; providing a second film substrate having a second thickness that is less than a thickness of the first film substrate; aligning the first film substrate with the second film substrate; bonding the first film substrate to the second film substrate around an outer edge and around an inner edge, the inner edge shaped to fit around a nose and mouth of a patient; cutting the first film substrate and the second film substrate around the outer edge and the inner edge of the first film substrate and the second film substrate such that a cutout is formed within the inner edge of the first film substrate and the second film substrate. The bonded and cut first film substrate and second film substrate form a first sheet that is joined to a second sheet. The shell is joined to the first sheet at the surface formed on the bottom of the flange.

In a third aspect, a method of manufacturing a mask includes: providing a shell having an inlet formed on a body of the shell and a flange formed around a lower end of the body, the flange forming a surface on a bottom thereof; providing a first film substrate formed of blow molded TPU film having a first thickness; providing a second film substrate formed of blow molded TPU film having a second thickness that is less than a thickness of the first film substrate; aligning the first film substrate with the second film substrate; bonding the first film substrate to the second film substrate around an outer edge and around an inner edge, the inner edge shaped to fit around a nose and mouth of a patient; cutting the first film substrate and the second film substrate around the outer edge and the inner edge of the first film substrate and the second film substrate such that a cutout is formed within the inner edge of the first film substrate and the second film substrate. The bonded and cut first film substrate and second film substrate form a first sheet that is joined to a second sheet. The shell is joined to the first sheet at the surface formed on the bottom of the flange.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Embodiments herein include methods of manufacturing a mask 10 (FIG. 1), the mask 10 preferably used for anesthesia and covering a nose and mouth of a patient. The face mask 10 preferably includes an upper shell 12 and a lower air cushion 14 attached thereto. The upper shell 12 is preferably formed of a material that is more rigid than a material of the lower air cushion 14. The upper shell 12 includes an inlet 16 for receiving a gas to be administered to the patient. The lower air cushion 14 is preferably bonded to the upper shell 12 and is shaped to fit over a nose and mouth of the patient to administer anesthesia to the patient through the mask 10. Methods and the resulting mask 10 disclosed herein advantageously provide for ease of manufacturing the mask 10 that is both inexpensive and forms a tight seal against the patient's face for proper administration of anesthesia to the patient.

Figure 1:
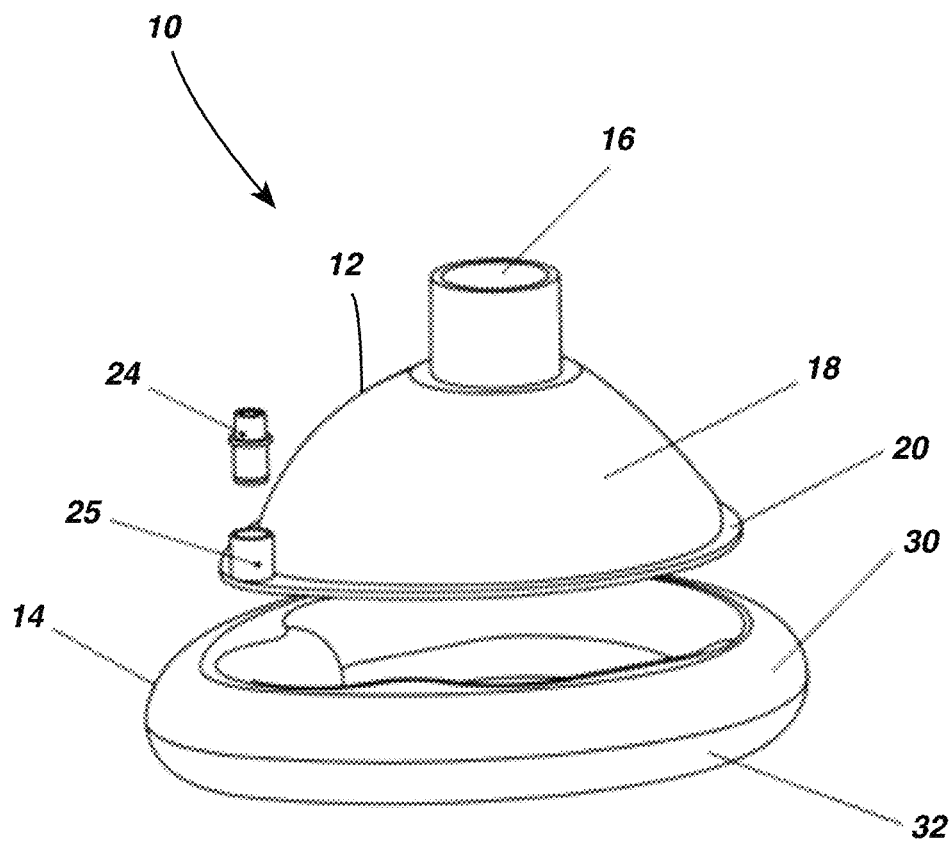
FIG. 1 shows an exploded view of a mask according to one embodiment of the present disclosure.
Figure 3:
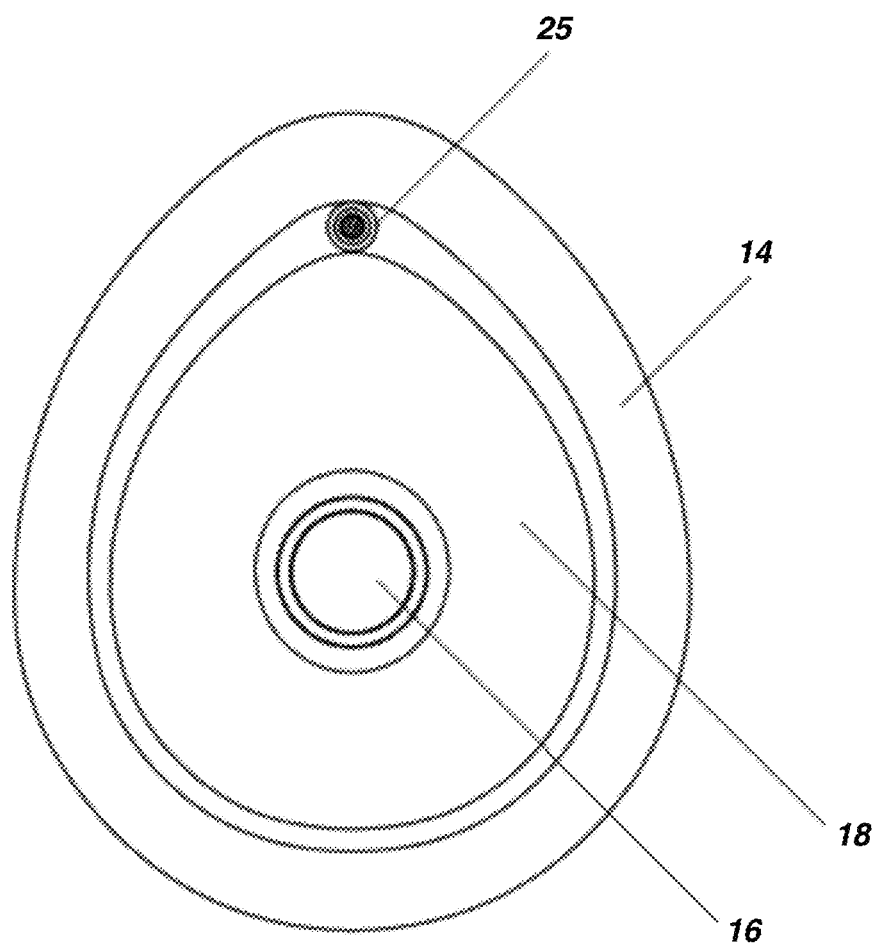
FIG. 3 shows a bottom view of a mask according to one embodiment of the present disclosure.

With further reference to FIG. 1, the inlet 16 is preferably located on a top of the upper shell 12 and is in fluid communication with an interior of the upper shell 12. The upper shell 12 includes a body 18 that is preferably conical in shape. A flange 20 is preferably located around a bottom end of the body 18 of the shell 12. The flange 20 forms a flat surface 22 (FIG. 3) on an underside thereof for bonding the upper shell 12 to the lower air cushion 14 as described in greater detail below.

The upper shell 12 may further include an air valve 24 formed thereon. The air valve 24 is preferably a check valve in fluid communication with an interior of the lower air cushion 14 for receiving air in the lower air cushion 14 that may allow air to enter or escape the lower air cushion 14. The air valve 24 is preferably located through an air valve channel 25 of the flange 20 of the upper shell 12 and communicates with an interior of the lower air cushion 14 such that air or other gases may be used to inflate the lower air cushion 14. The air valve 24 retains the air or other gases within the lower air cushion 14 to keep the lower air cushion 14 substantially inflated when in use with a patient. In one embodiment, the air valve 24 is formed with a Luer fitting such that the air valve 24 is readily connected to a pump or other device for adding air or other gases to inflate the lower air cushion 14.

The upper shell 12 is preferably formed according to known methods of molding upper portions of anesthesia masks. In a preferable embodiment, the upper shell 12 is molded from a plastic or other polymer or composite such that the upper shell 12 is more rigid than materials forming the lower air cushion 14 described below. In one preferable embodiment, the upper shell is formed of injection molded polyvinyl chloride (PVC) that may include additional compounds such as plasticizers such that the upper shell 12 is substantially resilient yet flexible. The upper shell 12 may be formed of other various suitable materials, such as polycarbonate.

Figure 4:
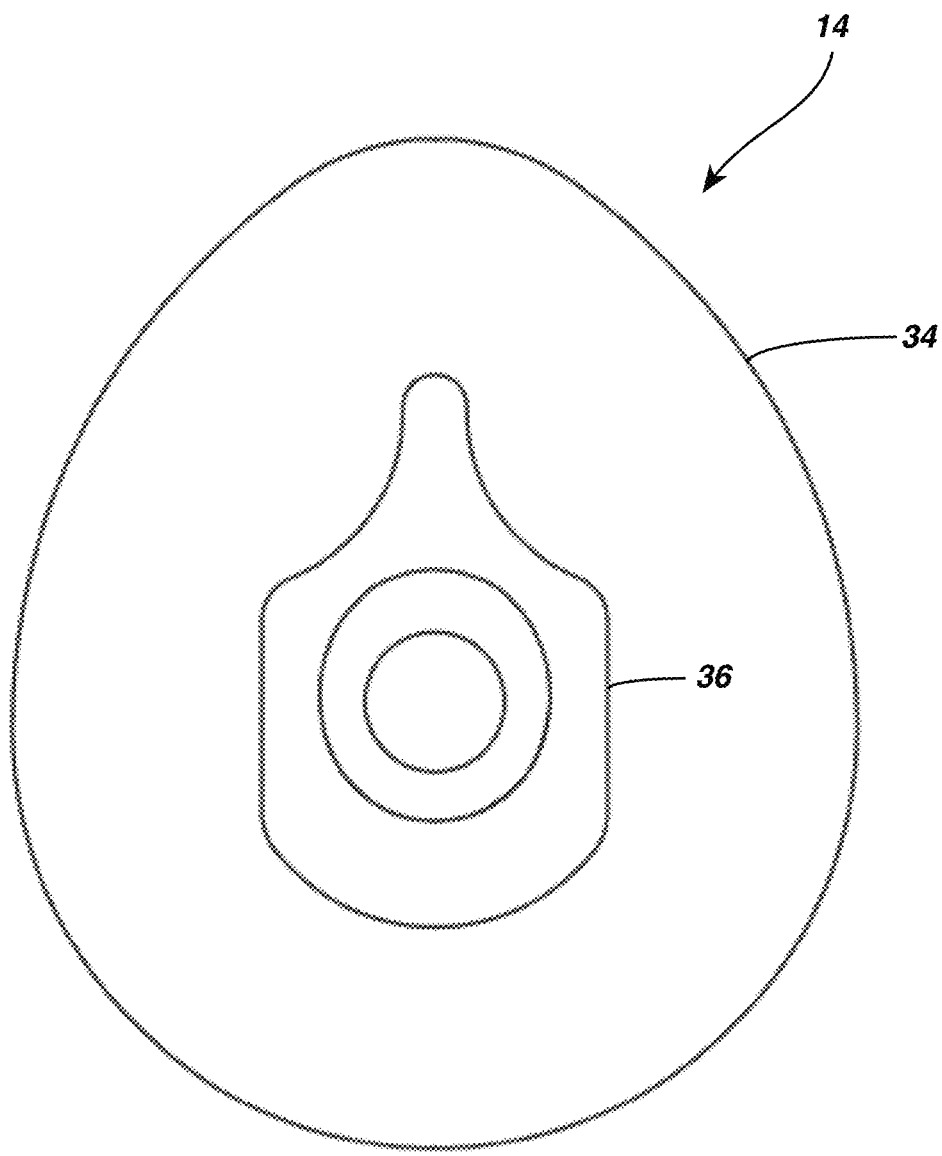
FIG. 4 shows a cross-sectional view of a lower cushion of a mask according to one embodiment of the present disclosure.
Figure 5:
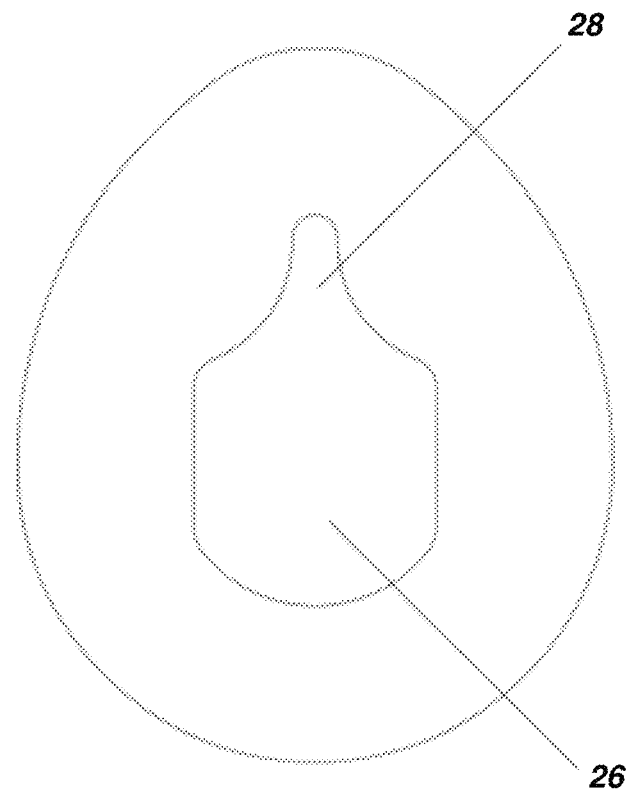
FIG. 5 shows a top plan view of one of a first sheet or second sheet of an air cushion according to one embodiment of the present disclosure.
Figure 6:
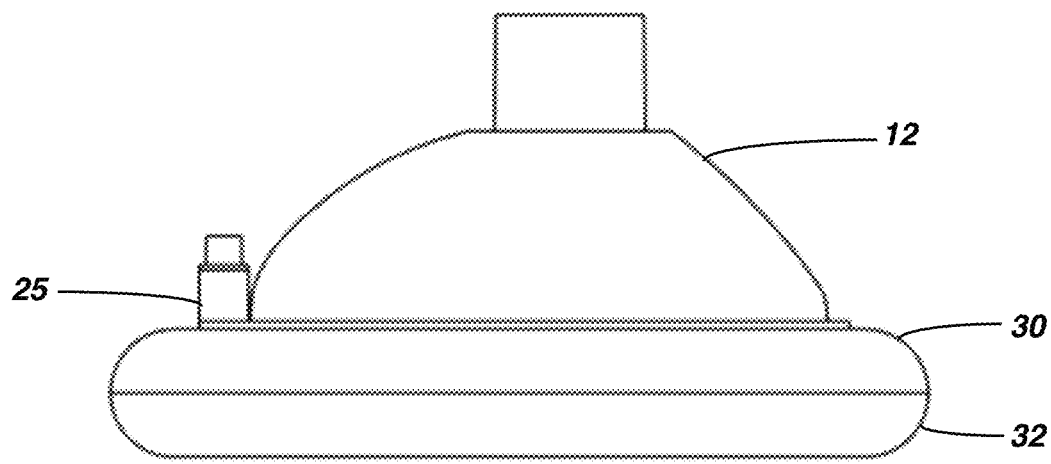
FIG. 6 shows a side view of a mask according to one embodiment of the present disclosure.
Figure 7:
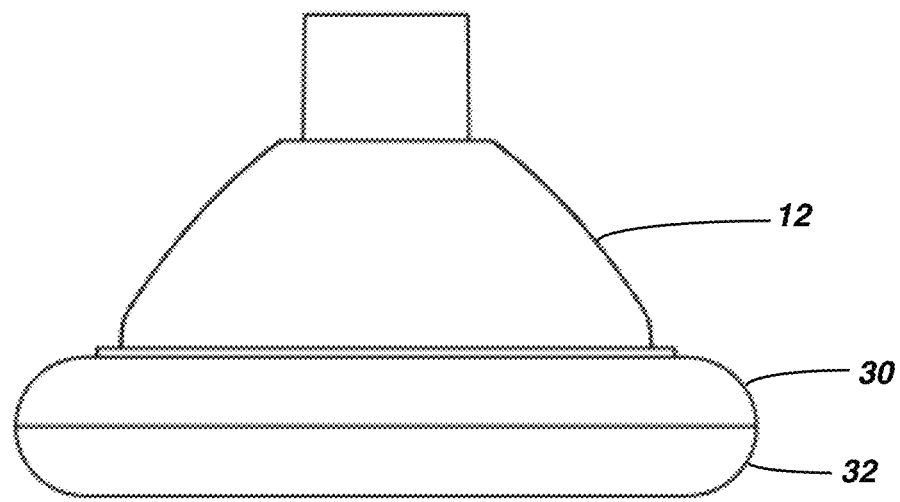
FIG. 7 shows a rear view of a mask according to one embodiment of the present disclosure.

The lower air cushion 14 is preferably bonded to the flat surface 22 of the flange 20 according to methods described herein. Referring to FIG. 4, the lower air cushion 14 is preferably ovular in shape and includes an open inner portion for fitting around a nose and mouth of a patient when the mask 10 is placed on the patient's face. The open inner portion includes a mouth portion 26 for fitting around a mouth of the patient and a contoured portion 28 for fitting around a nose of the patient when the mask 10 is placed on the patient's face. When inflated, the lower air cushion 14 expands in volume such that the lower air cushion 14 supports the upper shell 12 over the patient's face while providing a deformable surface against the patient's face to create a substantially air-tight seal against the patient's face and around the mouth and nose of the patient.

The lower air cushion 14 is preferably formed in at least two sections that are bonded together. In a preferable embodiment the lower air cushion 14 is formed from a first sheet 30 that is bonded to a second sheet 32. The first sheet 30 and second sheet 32 are preferably bonded along edges of the first sheet 30 and the second sheet 32 according to methods described herein. In a preferable embodiment, the first sheet 30 and the second sheet 32 are formed from blow molded processes. The first sheet 30 and the second sheet 32 are preferably formed from blow molded films of thermoplastic polyurethane (TPU) that are cut into shapes of the lower air cushion 14 described herein and bonded according to methods described below. In one embodiment, the first sheet 30 is formed from a film of material that has a thickness that is greater than a thickness of the second sheet 32 such that the first sheet 30 provides a sturdy bonding surface for the upper shell 12 while the second sheet 32 provides a softer and more deformable surface for contact with the patient's face. The first sheet 30 and the second sheet 32 preferably have a thickness of from about 0.02 mm to about 0.2 mm.

While embodiments describe use of blow molded TPU film, it is also understood that various other materials may be suitable for embodiments of the air cushion 14 described herein. For example, the first sheet 30 and the second sheet 32 may be selected from polyvinyl chloride (PVC), ethylene-vinyl acetate (EVA), or combinations thereof. Other suitable materials may be used having desirable characteristics for the air cushion 14, such as being pliable, transparent, low gas permeability, capable of being bonded with common glues or solvents, elastic, heat sealable, able to withstand heat up to approximately 80° C., soft to touch, and resiliency to discoloration over time.

In one embodiment, the first sheet 30 is formed of a first material and the second sheet 32 is formed of a second material. In another particular embodiment, the first sheet of material 32 may be formed of a first material that is different than a second material of the second sheet 32. For example, the first sheet 32 may be formed of a more durable material for bonding the first sheet 32 of the lower air cushion 14 to the upper shell 12. The second sheet 32 may be formed of a different material that is more pliable or otherwise suitable for contacting a face of the patient.

Referring to FIG. 4, the lower cushion 14 has an outer edge 34 and an inner edge 36 formed thereon. The inner edge 36 is formed having the mouth portion 26 and the contoured portion 28 such that a cutout formed in a center of the lower cushion 14 fits around the nose and mouth of the patient.

Embodiments herein include methods of manufacturing the mask 10. In particular, methods include efficiently manufacturing the lower air cushion 14 formed of the first sheet 30 and the second sheet 32 that are joined together and bonded to the upper shell 12 to create a mask 10 that is deformable to the patient's face while also sufficiently durable to withstand joining of the lower air cushion 14 to the shell 12.

Methods of manufacturing the mask 10 having the lower air cushion 14 formed of the first sheet 30 and the second sheet 32 include providing the shell 12, such as a pre-formed shell 12 that is manufactured prior to assembly of the mask 10 described herein. The shell 12 is preferably separately formed according to known methods of molding or otherwise manufacturing the shell 12. The shell 12 is preferably formed of a polymer that is more rigid or less deformable than either of the first sheet 30 and the second sheet 32.

A first film substrate is selected for forming the first sheet 30 and a second film substrate is selected for forming the second sheet 32. In one preferable embodiment, the second film substrate has characteristics that are different from the first film substrate. For example, the first film substrate may have a thickness that is greater than a thickness of the second film substrate. Alternatively, the first film substrate may be formed of a first type of material while the second film substrate is formed of a second type of material. In a preferable embodiment, the first film substrate has a thickness that is greater than a thickness of the second film substrate such that the first film substrate may withstand bonding of the lower air cushion 14 to the shell 12.

A mold is preferably provided having pre-formed inner and outer contours. The mold may be, for example, a hot cutting mold, high frequency mold, or ultrasonic mold. The mold includes outer contours that are shaped to match a shape of outer edges of the lower air cushion. The inner contours of the mold are shaped to match a shape of inner edges of the lower air cushion, including the mouth portion 26 and the contoured portion 28 of the lower air cushion 14.

The first film substrate and the second film substrate are fed into the mold. The first film substrate and the second film substrate are preferably fed into the mold such that the first film substrate and the second film substrate are aligned with one another in the mold. For example, the first film substrate and the second film substrate are preferably aligned such that planar portions of the films are in contact with one another. The first film substrate and second film substrate are preferably aligned in contact with one another such that substantially no air is trapped between the first film substrate and the second film substrate prior to cutting or stamping methods described below.

The first film substrate and the second film substrate are subsequently cut or stamped and bonded with one another on the mold. In a preferable embodiment, a fully automated hot melt press is used such that hot melt welding and stamping are performed simultaneously. A temperature of the hot melt press preferably exceeds a melting temperature of at least one of the first film substrate and the second film substrate. The hot melt press welds the first film substrate to the second film substrate along the pre-formed inner and outer contours of the mold. Further, the hot melt press stamps the first film substrate and the second film substrate into a desirable shape for the lower air cushion 14. The resulting joined first film substrate and the second film substrate are subsequently shaped and joined into the first sheet 30 and the second sheet 32 that form the lower air cushion 14.

In one embodiment, to avoid melted portions of the first film substrate and the second film substrate from sticking or otherwise bonding to the mold, a high-temperature non-stick material may be added during molding and stamping, such as by locating the material between the mold and the first film substrate and the second film substrate prior to stamping and molding of the substrates.

In a next step, the first sheet 30 and the second sheet 32 joined together and forming the lower air cushion 14 are secured to the upper shell 12. In a preferred embodiment, the first sheet 30 is bonded to the flange 20 of the upper shell 12, such as with an adhesive or solvent.

After stamping and molding the first film substrate and the second film substrate into the first sheet 30 and the second sheet 32 joined thereto, an aperture is pierced in the first sheet 30 at a location on the first sheet 30 such that the aperture aligns with the air valve 24 of the upper shell 12 when the lower air cushion 14 is joined to the upper shell 12. In a preferable embodiment, the first sheet 30 is pierced after bonding to the upper shell 12. In a preferred embodiment, a piercing tool is inserted through the air valve channel 25 and into contact with the first sheet 30 to pierce the first sheet 30. However, it is also understood that the first sheet 30 may be pierced prior to bonding to the upper shell 12.

EXAMPLE

In one exemplary embodiment, the mask 10 described above is formed having the lower air cushion 14 including the first sheet 30 and the second sheet 32 bonded thereto. TPU film is provided as the first film substrate and the second film substrate for forming the resulting first sheet 30 and the second sheet 32. The first film substrate preferably has a thickness of approximately 0.1 mm and the second film substrate preferably has a thickness of approximately 0.05 mm. The first film substrate is thicker such that the resulting first sheet 30 is better able to withstand any dissolving effect of a solvent bond. The second film substrate is thinner than the first film substrate such that the resulting second sheet 32 is thinner to create a softer and more pliable surface for contacting the patient's face when the mask 10 is in use.

A steel die is heated to a temperature that is above a melting temperature of the TPU material used for the first film substrate and the second film substrate. For example, the steel die may be heated to a temperature of approximately 180° C. and subsequently pressed down onto the aligned first film substrate and the second film substrate. The steel die is preferably applied to the first film substrate and the second film substrate for a duration of between about 0.1 and 5 seconds, and more preferably for a duration of approximately 1.5 seconds. The first film substrate and the second film substrate are melted together in a shape of contours of the die, such as the preferred shape of the lower air cushion 14 described above.

To avoid adherence of the first film substrate and the second film substrate to the die, a high-temperature non-stick material, such a thin sheet or woven fabric coated with PTFE, is inserted between the die and the first film substrate and the die and the second film substrate. In one embodiment, a sheet of woven fiberglass coated with PTFE is fed into the die with the first film substrate and the second film substrate. The PTFE coated fabric may be inserted between the die and the first film substrate and subsequently removed with the bonded first sheet 30 and the second sheet 32.

Figure 2:
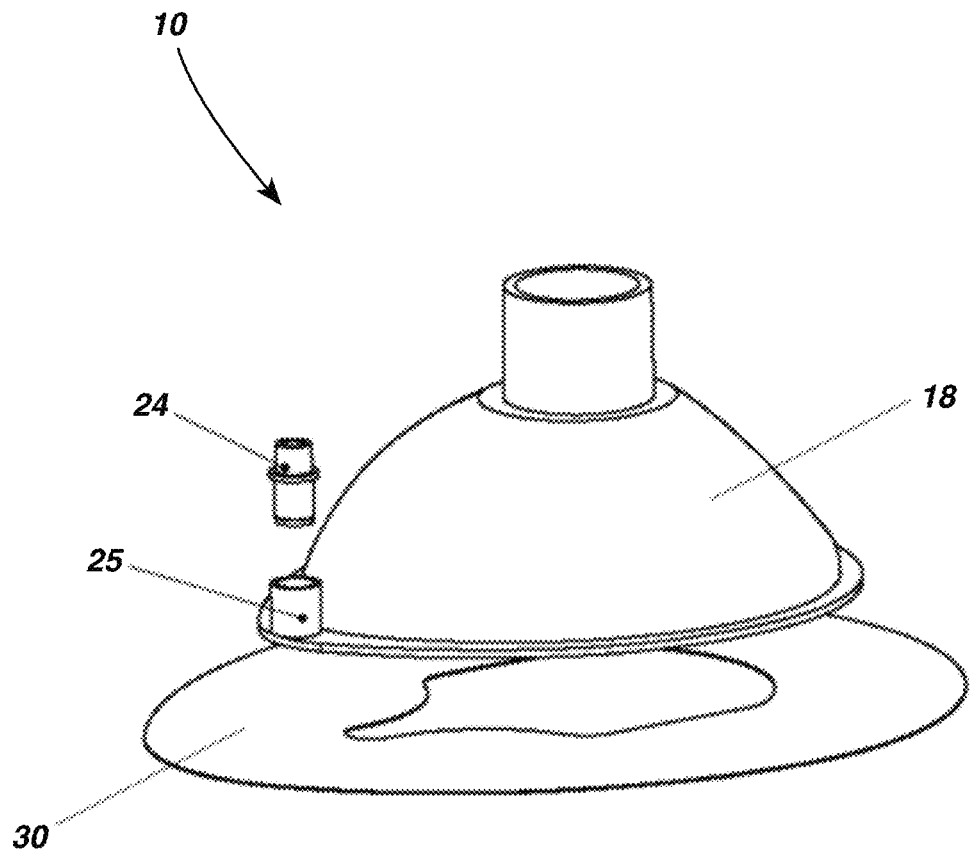
FIG. 2 shows an exploded view of a mask and lower cushion during manufacturing of the mask according to one embodiment of the present disclosure.

Cutting and melting together of the first film substrate and the second film substrate forms the shape of the lower air cushion 14. The resulting shaped first sheet 30 and second sheet 32 are subsequently bonded to the flange 20 of the upper shell 12 with a glue or solvent bonded with a solvent bonding agent, such as tetrahydrofuran (THF). The resulting shaped air cushion 14 contains no air between the first sheet 30 and the second sheet 32, as shown in FIG. 2.

An aperture is pierced in the first sheet 30 in alignment with the air valve 24 of the shell 12. The aperture may be formed by melting the aperture through the first sheet 30. Alternatively, the aperture may be formed such as by piercing the first sheet 30 with a tool. Melting or forming of the aperture is such that only the first sheet 30 is pierced or melted without piercing or melting a whole through the second sheet 32.

After bonding the lower air cushion 14 to the upper shell 12, an air valve is inserted into the upper shell 12. When in use, the lower cushion 14 of the mask 10 may be inflated, such as by using a Luer syringe connected to the air valve. The air valve prevents air from escaping the lower air cushion 14 during use.

The mask 10 and methods of forming the mask 10 described herein advantageously provide a mask that is both comfortable while also being sufficiently resilient and readily manufactured. By preferably using blow molded plastic films of TPU, the lower air cushion 14 may be rapidly manufactured relative to rotational molding and other existing methods of manufacturing masks. Further, blow molded plastic films may be produced having tight tolerances and relatively thin thickness, thereby avoiding challenges typically associated with forming the portion of masks that is in contact with a patient's face from melted plastic. The use of TPU film is also advantageous because TPU blown film has virtually no detectable odor. Existing products formed of plastic typically require a scent additive to cover up odors associated with plastic masks. The use of TPU blown film therefore significantly reduces odors and further decreases expenses relative to use of an additive. Yet another advantage of forming the first sheet 30 having a thickness greater than a thickness of the second sheet 32 is improved permeability of the mask.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method of manufacturing a mask, the method comprising:
   providing a shell having an inlet formed on a body of the shell and a flange formed around a lower end of the body, the flange forming a surface on a bottom thereof;
   providing a first film substrate sheet;
   providing a second film substrate sheet;

aligning the first film substrate sheet with the second film substrate sheet such that substantially no air is trapped between the first film substrate and the second film substrate;

bonding the first film substrate sheet to the second film substrate sheet around an outer edge and around an inner edge, the inner edge bonded in a shape of a cutout to fit around a nose and mouth of a patient;

cutting the first film substrate sheet and the second film substrate sheet around the outer edge and the inner edge of the first film substrate sheet and the second film substrate sheet such that the cutout is formed within the inner edge of the first film substrate sheet and the second film substrate sheet; and joining the shell to the first film substrate sheet at the surface formed on the bottom of the flange of the shell.

2. The method of claim 1, wherein the shell is formed of a plastic that is more rigid than a material of the first film substrate sheet and the second film substrate sheet.

3. The method of claim 1, wherein the first film substrate sheet and the second film substrate sheet comprise blown TPU film.

4. The method of claim 1, wherein the bonding and cutting of the first film substrate sheet to the second film substrate sheet around the outer edge and the inner edge occurs simultaneously.

5. The method of claim 1, the shell further comprising an air valve formed in the body of the shell.

6. The method of claim 5, further comprising piercing an aperture in the first film substrate sheet such that the aperture is in alignment with the air valve of the shell when the first film substrate sheet is joined to the flange of the shell.

7. The method of claim 1, wherein the cutout within the inner edge includes a mouth portion and a nose contour such that the cutout fits around the nose and mouth of the patient.

8. The method of claim 1, wherein the first film substrate sheet and the second film substrate sheet are formed of a material selected from the group consisting of TPU, PVC, EVA, and combinations thereof.

9. The method of claim 1, wherein the bonding of the first film substrate sheet and the second film substrate sheet is performed by melting the first film substrate sheet to the second film substrate sheet along the outer edge and inner edge.

10. The method of claim 1, wherein the bonding of the first film substrate sheet and the second film substrate sheet is performed by ultrasonic welding of the first film substrate sheet to the second film substrate sheet along the outer edge and the inner edge.

11. The method of claim 1, wherein the first film substrate sheet and the second film substrate sheet have a thickness of from about 0.02 mm and 0.2 mm.

12. The method of claim 11, the first film substrate sheet having a thickness of from about 0.08 mm and about 0.12 mm and the second film substrate sheet having a thickness of from about 0.03 mm to about 0.07 mm.

13. The method of claim 12, the first film substrate sheet having a thickness of approximately 0.1 mm and the second film substrate sheet having a thickness of approximately 0.05 mm.

14. The method of claim 1, wherein a material of the first film substrate sheet differs from a material of the second film substrate sheet.

15. A method of manufacturing a mask, the method comprising:

providing a shell having an inlet formed on a body of the shell and a flange formed around a lower end of the body, the flange forming a surface on a bottom thereof;

providing a first film substrate sheet having a first thickness;

providing a second film substrate sheet having a second thickness that is less than a thickness of the first film substrate sheet;

aligning the first film substrate sheet with the second film substrate sheet, such that substantially no air is trapped between the first film substrate and the second film substrate;

bonding the first film substrate sheet to the second film substrate sheet around an outer edge and around an inner edge, the inner edge bonded in a shape of a cutout to fit around a nose and mouth of a patient;

cutting the first film substrate sheet and the second film substrate sheet around the outer edge and the inner edge of the first film substrate sheet and the second film substrate sheet such that the cutout is formed within the inner edge of the first film substrate sheet and the second film substrate sheet; and joining the shell to the first sheet at the surface formed on the bottom of the flange.

16. A method of manufacturing a mask, the method comprising:

providing a shell having an inlet formed on a body of the shell and a flange formed around a lower end of the body, the flange forming a surface on a bottom thereof;

providing a first film substrate sheet formed of blown TPU film having a first thickness;

providing a second film substrate sheet formed of blown TPU film having a second thickness that is less than a thickness of the first film substrate sheet;

aligning the first film substrate sheet with the second film substrate sheet, such that substantially no air is trapped between the first film substrate and the second film substrate;

bonding the first film substrate sheet to the second film substrate sheet around an outer edge and around an inner edge, the inner edge bonded in a shape of a cutout to fit around a nose and mouth of a patient;

cutting the first film substrate sheet and the second film substrate sheet around the outer edge and the inner edge of the first film substrate sheet and the second film substrate sheet such that the cutout is formed within the inner edge of the first film substrate sheet and the second film substrate sheet; and joining the shell to the first sheet at the surface formed on the bottom of the flange.

* * * * *